(12) United States Patent
Mijers et al.

(10) Patent No.: US 9,901,676 B2
(45) Date of Patent: Feb. 27, 2018

(54) BIDIRECTIONAL VALVE WITH IMPROVED THRESHOLD PRESSURE ACCURACY

(71) Applicant: ILLINOIS TOOL WORKS INC., Glenview, IL (US)

(72) Inventors: Jan W. M. Mijers, Holland (NL); Colm M. Carmody, Co. Kerry (IE)

(73) Assignee: ILLINOIS TOOL WORKS INC., Glenview, IL (US)

(*) Notice: Subject to any disclaimer, the term of this patent is extended or adjusted under 35 U.S.C. 154(b) by 147 days.

(21) Appl. No.: 14/899,088

(22) PCT Filed: May 6, 2014

(86) PCT No.: PCT/US2014/036889
§ 371 (c)(1),
(2) Date: Dec. 16, 2015

(87) PCT Pub. No.: WO2014/204586
PCT Pub. Date: Dec. 24, 2014

(65) Prior Publication Data
US 2016/0129181 A1 May 12, 2016

Related U.S. Application Data

(60) Provisional application No. 61/835,821, filed on Jun. 17, 2013.

(51) Int. Cl.
*A61M 39/24* (2006.01)
*A61M 5/168* (2006.01)
(Continued)

(52) U.S. Cl.
CPC ... *A61M 5/16813* (2013.01); *A61B 5/150221* (2013.01); *A61B 5/150229* (2013.01);
(Continued)

(58) Field of Classification Search
CPC ............ A61M 39/24; A61M 2039/242; A61M 39/223; A61M 2039/2493; A61M 39/22;
(Continued)

(56) References Cited

U.S. PATENT DOCUMENTS 4,317,467 A    3/1982  Heyland
4,696,448 A *  9/1987  Mazloom ................ B60R 7/084
                                              224/277

(Continued)

FOREIGN PATENT DOCUMENTS

EP    0934757 A2    8/1999
WO   2005123176 A1  12/2005
WO   2011151090 A1  12/2011

OTHER PUBLICATIONS

ISR for PCT/US2014/036889 dated Nov. 6, 2014.

*Primary Examiner* — Gerald Landry, II

(57) ABSTRACT

A bidirectional valve for medical use or the like provides different threshold opening pressures in different directions using a valve seat and flapper construction providing improved characterization in operation in contrast to cross-slit valves often used for bidirectional operation. A valve disk supported in a central annular region provides movable portions engaging in valve seats at a peripheral region and a central region.

17 Claims, 6 Drawing Sheets

(51) Int. Cl.
*A61B 5/15* (2006.01)
*A61M 39/22* (2006.01)

(52) U.S. Cl.
CPC ....... *A61B 5/150992* (2013.01); *A61M 39/24* (2013.01); *A61M 39/223* (2013.01); *A61M 2039/242* (2013.01); *A61M 2039/246* (2013.01); *A61M 2039/2446* (2013.01)

(58) Field of Classification Search
CPC .............. A61M 39/26; A61M 5/16881; A61M 2039/2433; A61M 2039/2446
USPC ........... 137/493, 512.4, 843, 852; 604/99.02, 604/99.03, 246, 247
See application file for complete search history.

(56) References Cited

U.S. PATENT DOCUMENTS

| | | | | |
|---|---|---|---|---|
| 5,992,462 A * | 11/1999 | Atkinson | ............... | A61M 39/24 137/515.5 |
| 6,089,272 A | 7/2000 | Brand et al. | | |
| 6,708,714 B1 * | 3/2004 | Mijers | ................... | A61M 39/24 137/102 |
| 7,360,556 B2 * | 4/2008 | Mijers | ................... | F16K 15/144 137/493.9 |
| 7,673,653 B2 * | 3/2010 | Mijers | ................... | F16K 15/144 137/843 |
| 7,681,750 B2 * | 3/2010 | Jackel | ................... | B65D 47/06 215/235 |
| 2004/0188541 A1 * | 9/2004 | Maruyama | ............... | B60S 1/481 239/284.1 |
| 2007/0163656 A1 * | 7/2007 | Mijers | ................... | F16K 15/144 137/493.9 |
| 2007/0163664 A1 * | 7/2007 | Mijers | ................... | F16K 15/144 137/859 |
| 2008/0087859 A1 * | 4/2008 | Enerson | ................ | F16K 15/141 251/149.7 |
| 2008/0169444 A1 * | 7/2008 | Guala | ................... | A61M 39/24 251/331 |
| 2010/0268156 A1 * | 10/2010 | Milacek | ............. | A61B 17/3415 604/30 |
| 2012/0078197 A1 * | 3/2012 | O'Connor | ............. | A61M 39/24 604/247 |
| 2013/0112302 A1 * | 5/2013 | Fukano | ................. | F16K 15/144 137/843 |
| 2013/0115117 A1 * | 5/2013 | Gonzalez-Moratiel Alvarez ...... | | F04B 43/0736 417/395 |
| 2014/0014202 A1 * | 1/2014 | Keren | ....................... | F16K 7/17 137/510 |
| 2014/0299212 A1 * | 10/2014 | Colm | .................... | A61M 39/24 137/843 |

* cited by examiner

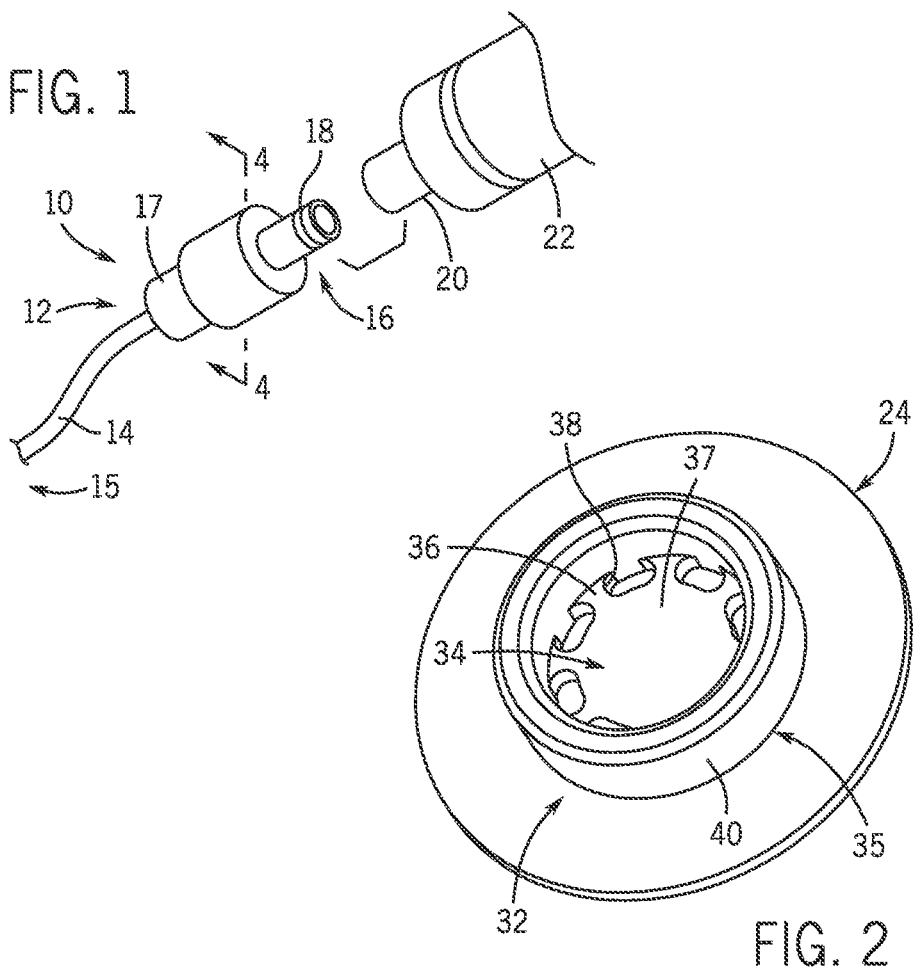
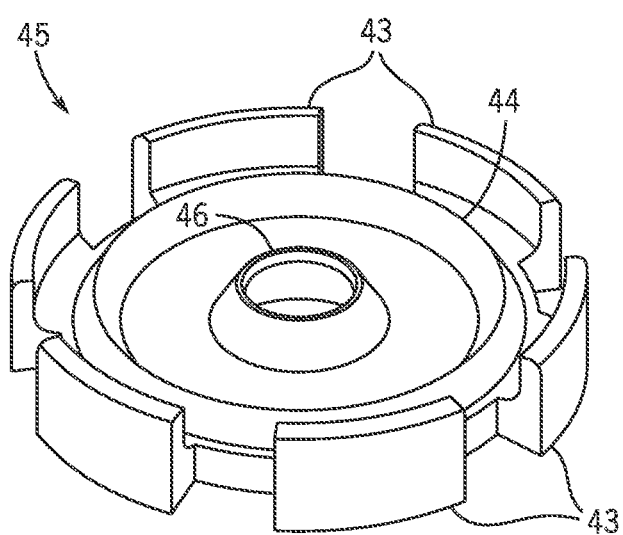

BIDIRECTIONAL VALVE WITH IMPROVED THRESHOLD PRESSURE ACCURACY

CROSS-REFERENCE TO RELATED APPLICATIONS

The present invention is a National Phase of International Application Number PCT/US2014/036889 filed May 6, and claims the benefit of U.S. provisional application Number 61/835,821 filed Jun. 17, 2013 and hereby incorporated by reference.

FIELD OF THE INVENTION

The present invention relates to normally closed valves providing for bidirectional flow above predetermined pressures.

BACKGROUND OF THE INVENTION

Vascular access catheters may be inserted into a patient to permit the infusion of liquid and drugs into the patient's blood supply and for periodic sampling of the patient's blood. A needle-free system may provide a luer or similar connector at the distal end of the catheter to allow a syringe or IV set to be attached to or removed from the catheter as desired.

When the catheter is not connected to an infusion or sampling device, it is important that it can be closed to prevent the introduction of contaminants into or loss of blood out of the catheter. For this purpose, it is known to place a bidirectional valve in series with the luer connector that opens only under predetermined threshold pressures associated with infusion into the patient or sampling of blood from the patient.

A common bidirectional valve of this type provides a dome, for example, fabricated of silicon rubber, having a cross-slit that opens under pressure. The dome provides for different threshold pressures for opening the slit depending on the direction of flow, with flow into the concave side of the dome occurring at a lower pressure than flow into the convex side of the dome. Normally it is desired that the infusion threshold pressure be lower than the aspiration or blood sampling pressure.

When blood is drawn out through such a catheter valve, it is normally desired to flush the valve mechanism with a counter-flow of an infusion liquid such as saline solution. In this respect, it is important that the flushing saline flow occur along substantially the same path as that to which the blood flowed.

A slit dome valve provides a relatively simple mechanism to generate a bidirectional valve opening under different predetermined pressures associated with different flow directions. Nevertheless, fabrication of the slit valve can be problematic. If the slit is not cut perfectly, the resulting valve may leak under low pressure or exhibit significant variations in threshold pressure.

SUMMARY OF THE INVENTION

The present invention provides a normally closed bidirectional valve permitting different threshold pressures with direction of flow, yet avoiding the problems associated with cross slit dome and other similar slit valves. Different regions of a valve disk open and close against different valve seats providing two valve systems associated with different flow directions. The valve systems communicate with valve ports via an overlapping channeling system so that a path of sampled or aspirated blood is fully traversed by the counter-flowing path of flushing or infusing liquid to clean the valve of blood product.

Specifically, in one embodiment, the invention provides a normally closed bidirectional valve having a housing with a first and second port communicating with an internal housing volume. An elastomeric disk is disposed between the first and second port in the internal housing volume, and retained against the housing within an annular region of the elastomeric disk between a central region and an outer peripheral region. In this way, a central region and outer peripheral region of the valve disk are free to move with respect to the housing. The housing provides a first valve seat engaging the outer peripheral region of the elastomeric disk when the elastomeric disk is in a relaxed state and a second valve seat engaging the central region when the elastomeric disk is in a relaxed state. In addition, the housing provides first flow channels leading from the first port to the elastomeric disk to press the elastomeric disk against the second valve seat and to press the elastomeric disk away from the first valve seat when pressure at the first port is greater than pressure at the second port. The housing further provides second flow channels leading from the second port to the elastomeric disk to press the elastomeric disk against the first valve seat and to lift the elastomeric disk away from the second valve seat when pressure at the second port is greater than pressure at the first port.

It is thus a feature of at least one embodiment of the invention to provide a valve using a robust, easily manufacturable and well-defined valve seat and valve flapper combination as opposed to a less predictable and more difficult to manufacture cross slit dome valve design.

The elastomeric disk may interact with the first and second valve seats to provide for a first threshold opening pressure at which fluid flows between the first port and the second port and a second threshold opening pressure different from the first threshold opening pressure when the fluid flows between the second port and the first port.

It is thus a feature of at least one embodiment of the invention to provide improved control over the valve openings in different flow directions by providing distinct valve structures for those different flow directions.

The first threshold opening pressure may permit gravity flow of intravenous liquids from a standard IV bag.

It is thus a feature of at least one embodiment of the invention to provide an extremely low opening pressure suitable for infusion.

In addition or alternatively, the threshold opening pressure may be less than 20 millibars and the second threshold opening pressure is greater than 2 bars. In addition or alternatively, the difference between the first and second threshold opening pressures may be a factor greater than 100.

It is thus a feature of at least one embodiment of the invention to provide a valve that offers a large difference in threshold opening pressures depending on direction.

The elastomeric disk may be comprised of a first and second elastic material of different elasticity.

It is thus a feature of at least one embodiment of the invention to provide greater flexibility in setting different threshold opening pressures by providing the ability to control not only the geometry of the valve disk but also the valve disk materials.

The first elastic material of greater elasticity may form the outer peripheral region of the elastomeric disk contacting the first valve seat and the second elastic material of lesser elasticity may form the central region contacting the second valve seat.

It is thus a feature of at least one embodiment of the invention to provide a readily manufactured dual-material elastomeric disk having a relatively simple circumferential seam line.

The first flow channel may substantially overlap an entirety of the second flow channels to provide cleaning of the valve with flow from the first port.

It is thus a feature of at least one embodiment of the invention to provide a valve where infusion liquid may cleanse the valve of blood material after aspiration or blood sampling.

Fluid flow may enter the first port in a first direction toward a first side of the elastomeric disk and the valve may include a diverter wall directing flow from the first port opposite the first direction toward a second side of the elastomeric disk.

It is thus a feature of at least one embodiment of the invention to provide directed flushing in the contact regions of the valve operating during blood flow.

The elastomeric first and second valve seats may provide substantially circular and concentric contact lines between the valve seat and the elastomeric disk.

It is thus a feature of at least one embodiment of the invention to provide two distinct valve structures for different flow directions using a single elastomeric disk component.

The first and second valve seats may be ridges contacting opposite sides of the elastomeric disk.

It is thus a feature of at least one embodiment of the invention to provide a simple valve structure that can be realized with fewer components.

Other features and advantages of the invention will become apparent to those skilled in the art upon review of the following detailed description, claims and drawings in which like numerals are used to designate like features.

BRIEF DESCRIPTION OF THE DRAWINGS

FIG. 1 is a fragmentary perspective view of a bidirectional valve of the present invention providing, in one application, a needle-free connection to a syringe for drawing a blood sample;

FIG. 2 is a perspective view of an elastomeric disk used to provide bidirectional fluid control in a first embodiment of the invention;

FIG. 3 is a perspective view of a support for the elastomeric disk of FIG. 2;

Figure 4:
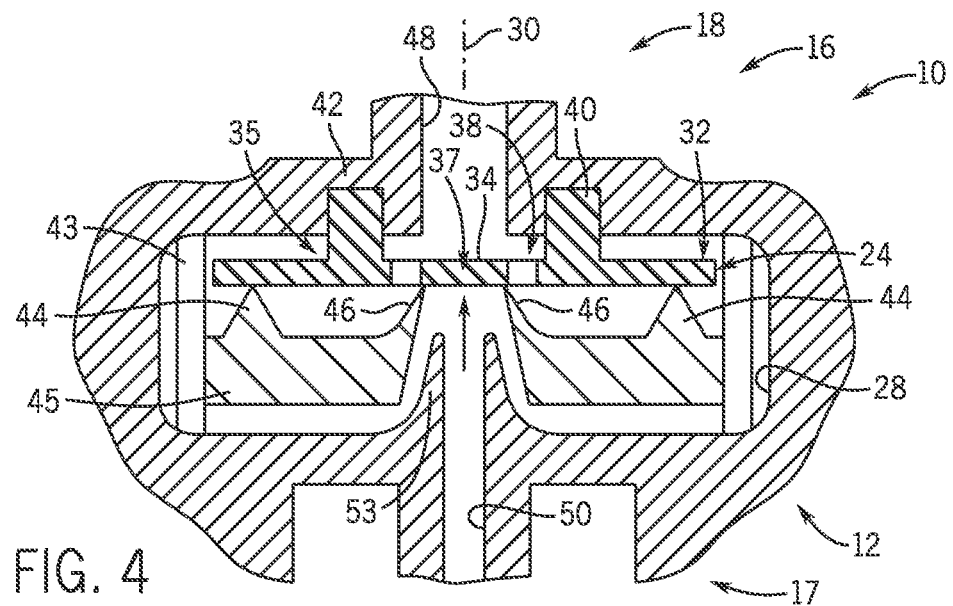
FIG. 4 is a cross-section along line 4-4 of FIG. 1 of the first embodiment of the invention showing a normal closed state of the valve.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE PREFERRED EMBODIMENTS

Referring now to FIG. 1, a bidirectional valve 10 per the present invention may be attached at a lower end 12 to a flexible catheter 14 communicating with a patient 15 (not shown) to provide for vascular access, for example, through a needle or the like placed in the patient 15. The lower end 12 of the bidirectional valve 10 may provide for a standard needle-free tubing connector 17, as known in the art, providing, for example, a tube of the flexible catheter 14 with a frustoconical outer surface receiving the IV line and expanding it into a barbed collar around the tube.

An upper end 16 of the bidirectional valve 10 may provide for a needle-free luer connector 18 such as a female luer lock or luer slip connector that may receive a corresponding connector 20 of a syringe 22, for example, for flushing, sampling or aspiration. Alternatively, the upper end 16 may receive a corresponding connector of an IV bag, infusion pump, or the like (not shown).

Referring now to FIGS. 2, 3 and 4, the valve 10 may provide a housing 42 constructed of one or more rigid components integrally molded or fixedly assembled together to define a cavity 28 positioned between an upper channel 48 of the needle-free luer connector 18 and a lower channel 50 of the needle-free tubing connector 17. Generally channels 48 and 50 are aligned and coaxial along an axis 30 and the cavity 28 positioned to receive and conduct fluid flow passing between needle-free luer connector 18 and needle-free tubing connector 17. The cavity 28 and housing 42 may be radially symmetric about axis 30.

The cavity 28 may include a flexible valve element, such as an elastomeric diaphragm 24, for example, fabricated of injection molded silicone rubber or the like. In this embodiment, the elastomeric diaphragm 24 may be a substantially planar circular disk extending generally perpendicular to an axis 30 of fluid flow and is centered and radially symmetric about that axis 30.

The elastomeric diaphragm 24 may provide an outer peripheral region 32 positioned around a central region 34. A mounting rim 40 may extend upward from an intermediate annular region 35, the latter separating the outer peripheral region 32 from the central region 34. The mounting rim 40 is received into a socket in the housing 42 to retain the intermediate annular region 35 substantially fixed with respect to the housing 42 while allowing the peripheral region 32 and central region 34 to move with respect to the housing 42.

The central region 34 in this case provides a circular blocking disk 37 attached to an inner edge of the intermediate annular region 35 through flexible struts 36. The flexible struts 36 extend radially and are separated to provide for flow passages 38 between the struts 36 within the inner edge of the intermediate annular region 35.

Natural resilience of the material of the elastomeric diaphragm 24 will hold a lower surface of the outer peripheral region 32 downward against an upwardly directed ridge of a valve seat 44, the latter extending in a ring about axis 30 beneath the outer peripheral region 32. The valve seat 44 may be supported by a support structure 45 separately molded and installed in the cavity 28 to be held between upper and lower cavity walls on peripheral crenellated flanges 43 which abut the upper cavity wall and lower cavity wall while providing for the passage of fluid between crenellations. The outer peripheral region 32 is outwardly cantilevered in a direction perpendicular to axis 30 and away from the mounting rim 40 of the intermediate annular region 35 so that it may flex upwardly away from the valve seat 44 or downwardly against the valve seat 44 depending on the direction of flow through the cavity 28 and the resulting differential pressure across the faces of the outer peripheral region 32.

The same natural resilience of the material of the elastomeric diaphragm 24 also will hold the blocking disk 37 of the central region 34 downward against an upwardly directed ridge of valve seat 46 extending in a ring concentrically within valve seat 44. The material of the valve seats 44 and 46 are fixed with respect to the cavity 28 but provide passages therearound as will be described.

Figure 5:
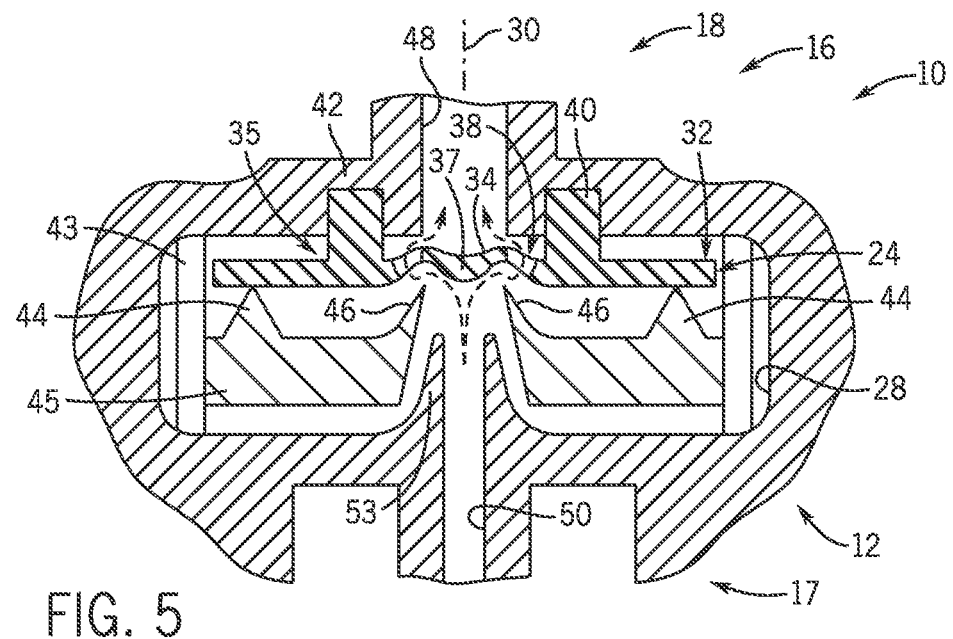
FIG. 5 is a figure similar to that of FIG. 4 showing deformation of a central region of the elastomeric disk to open the valve in a sampling/aspiration direction, for example, for the withdrawal of blood.

Referring now to FIG. 5, the upper channel 48 of the valve 10 may communicate with a syringe 22, for example, through a flow channel leading downward through the upper housing along axis 30 to the central region 34 of the elastomeric diaphragm 24. This flow channel may proceed through passages 38 around the edges of the blocking disk 37 to a flow region between valve seat 46 and valve seat 44. When an aspirating low pressure is applied to the upper channel 48, for example, by a syringe 22, the outer edge of blocking disk 37 and the corresponding struts 36 flex so that the outer edge of the blocking disk 37 rises away from valve seat 46 allowing fluid to be drawn through flow channels in the housing 42 from a lower channel 50, upward around the valve seat 46 and around the blocking disk 37 through the flow passages 38 into the upper channel 48. It will be appreciated that this flow only occurs when there is sufficient pressure difference between lower channel 50 and upper channel 48 to flex the central region 34 away from valve seat 46.

Figure 7:
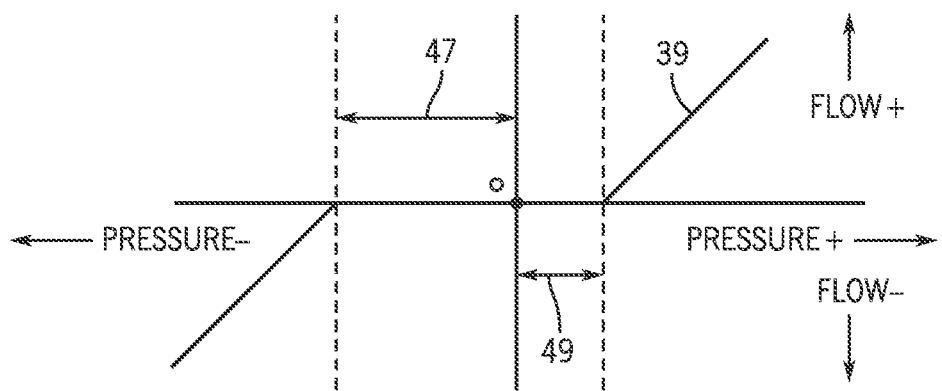
FIG. 7 is a plot of pressure as a function of flow through the valves of the present invention showing the ability to obtain different "cracking" pressures at which flow first begins with different directions of flow.

Referring to FIG. 7, the upward flow described above represents a negative pressure as depicted in FIG. 7 and requires threshold opening pressure 47 (cracking pressure) to be exerted against the blocking disk 37 before the blocking disk 37 will rise sufficiently from the valve seat 46 to allow passage of fluid through the passages 38 as indicated by graph line 39. When the magnitude of the negative pressure difference between lower channel 50 and upper channel 48 is below the necessary threshold opening pressure 47 needed to move the blocking disk 37, the central region 34 remains in contact with seat 46 preventing flow between channels 50 and 48.

Figure 6:
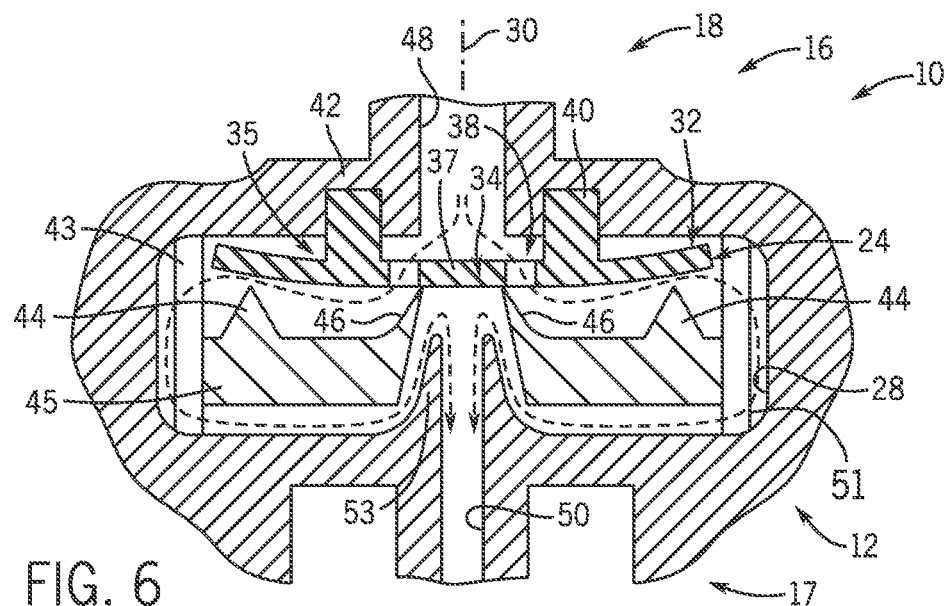
FIG. 6 is a figure similar to that of FIGS. 4 and 5 showing deformation of a an outer portion of the elastomeric disk to open the valve in a flushing/infusion direction.

Referring now to FIGS. 6 and 7, when the pressure in upper channel 48 rises above the pressure of lower channel 50 by a threshold opening pressure 49 such as may occur during a flushing or infusion process, and as represented by positive pressure in FIG. 7, flow from the upper channel 48 may pass through the flow passages 38 and into the region between the valve seats 46 and 44. This pressure causes an upward flexing of the outer rim of the outer peripheral region 32 causing it to rise away from valve seat 44 so that the flow may be received by a channel 51 passing beneath valve seats 46 and 44 into lower channel 50. Generally, the threshold opening pressure 49 will differ from that of 47 and will desirably be much lower. This permits a low-pressure infusion while requiring a higher pressure for reversing flow to sample blood or the like preventing accidental flow reversal with minor pressure spikes in the IV line, for example, when the patient coughs. A threshold opening pressure is a pressure in which flow first begins when flow pressure is slowly increased from zero in a given direction.

It will be noted that the path of fluid flow of FIG. 6 passes on both sides of valve seat 46 and the elastomeric diaphragm 24 contacting valve seat 46 to flush away accumulated blood despite the separation of the flow paths of flushing/infusion versus sampling/aspiration. This flushing process is enhanced by diverter walls 53 which cause the flow of fluid during flushing/infusion to reverse direction with respect to axis 30 to flow upward in a direction opposite the downward direction of flow of fluid entering the upper channel 48, for example, from an IV bag or the like.

The present valve design can also be used in other IV set applications requiring bidirectional flow, e.g., designs allowing for pressure relief should the pressure downstream of the valve become very high rather than the application of a low-pressure aspiration on needle-free luer connector 18.

Figure 8:
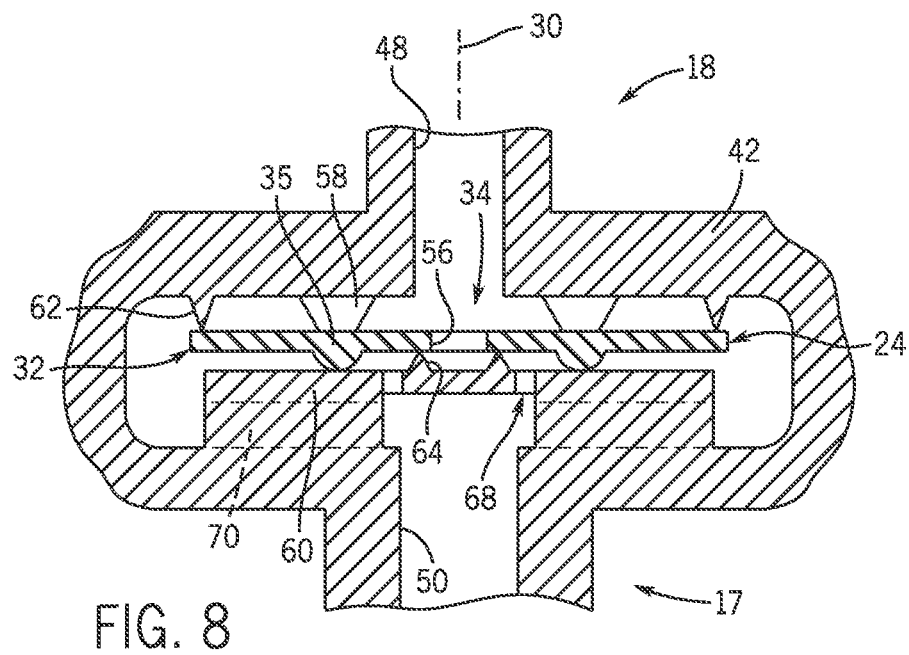
FIG. 8 is a figure similar to FIG. 4 of an alternative embodiment of the valve having fewer housing components and showing the normal closed state of the valve.

Referring now to FIG. 8, in an alternative embodiment, the central region 34 of the elastomeric diaphragm 24 may provide for a central circular opening 56 instead of the blocking disk 37 described above. As before an intermediate annular region 35 of the elastomeric diaphragm 24 may be stabilized against the housing 42 in this case by downwardly extending ribs 58 and upwardly extending ribs 60 cooperating with an increased thickness at the intermediate annular region 35.

In this embodiment, upwardly directed valve seat 44 is replaced with valve seat 62 extending downward from an upper wall of the housing 42 and in a ring about the axis 30 to abut and seal against the outer peripheral region 32 in a normal relaxed state. The central region 34 just outside of the opening 56, in a relaxed state, contacts valve seat 64 formed as part of the housing 42 and also extends in a ring about axis 30 concentrically within valve seat 62 and is directed upward to contact the lower surface of the central region 34. The valve seat 64 provides for multiple passages 68 around its periphery leading into lower channel 50 and is located directly beneath a portion of the elastomeric diaphragm 24 within the intermediate annular region 35 and outside of the valve seat 64.

Figure 9:
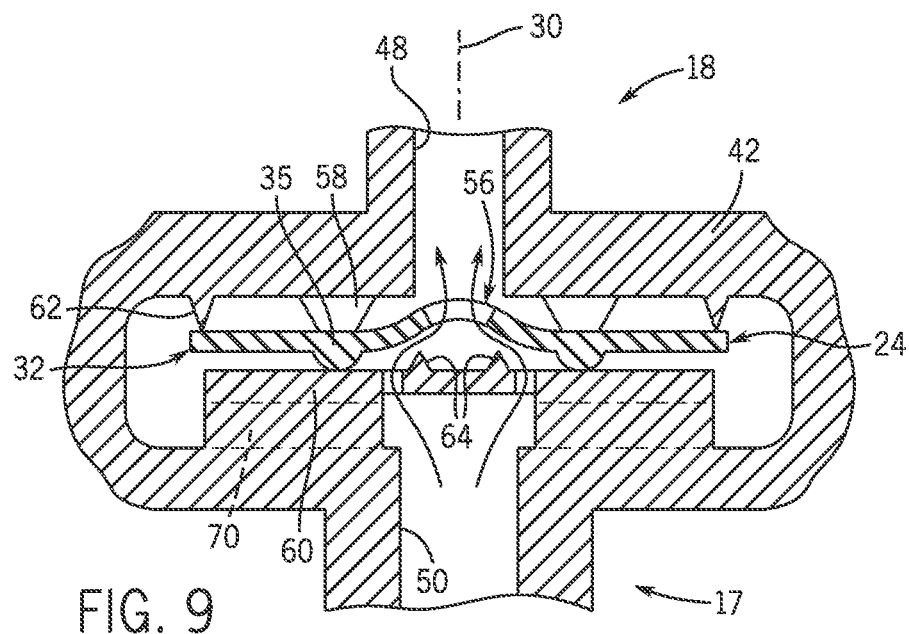
FIG. 9 is a figure similar to FIG. 8 showing deformation of the central region of the elastomeric disk to open the valve in a sampling/aspiration direction, for example, for the withdrawal of blood.

Referring now to FIG. 9, when a low pressure is applied on the upper central upper channel 48 of the valve 10 (with respect to the pressure in channel 50), the inner periphery of opening 56 rises upward away from the valve seat 64 allowing passage of fluid from the lower channel 50 through passages 68 and opening 56 into upper channel 48. As before, this flow only occurs when there is sufficient pressure difference between lower channel 50 and upper channel 48 to flex the central region 34 away from valve seat 46 thereby defining threshold opening pressure 47.

Figure 10:
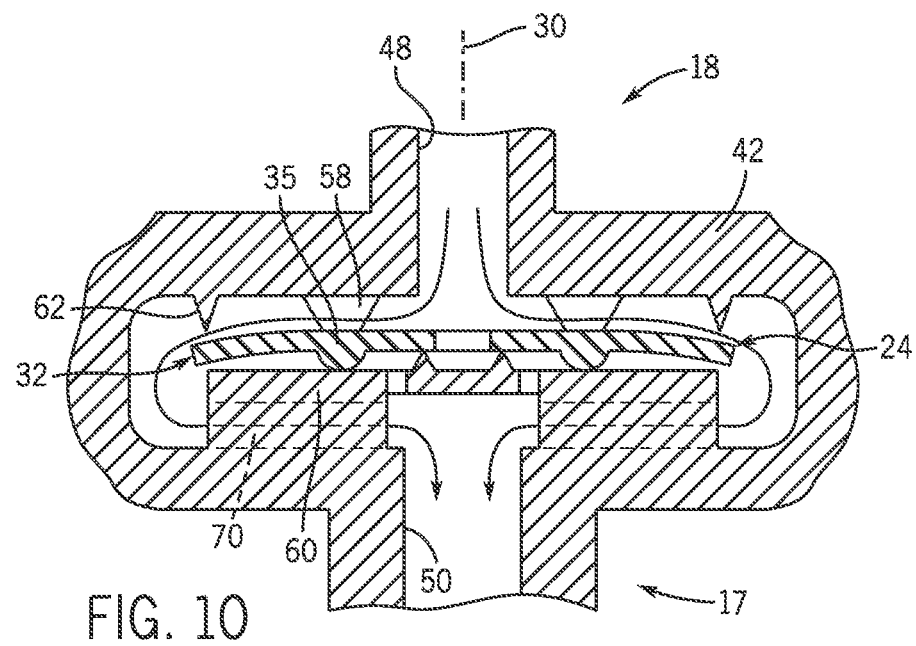
FIG. 10 is a figure similar to that of FIG. 8 showing deformation of an outer peripheral region of the elastomeric disk to open the valve in a flushing/infusion direction.

Referring to FIG. 10, when the pressure in upper channel 48 rises above the pressure of lower channel 50 by a threshold opening pressure 49 such as may occur during a flushing or infusion process, and as represented by positive pressure in FIG. 7, flow from the upper channel 48 may pass ribs 58 to press downward on the outer rim of the outer peripheral region 32 causing it to drop away from valve seat 62 so that the flow may be received by channel 70 passing radially between ribs 60 and providing a passageway into lower channel 50.

Figure 11:
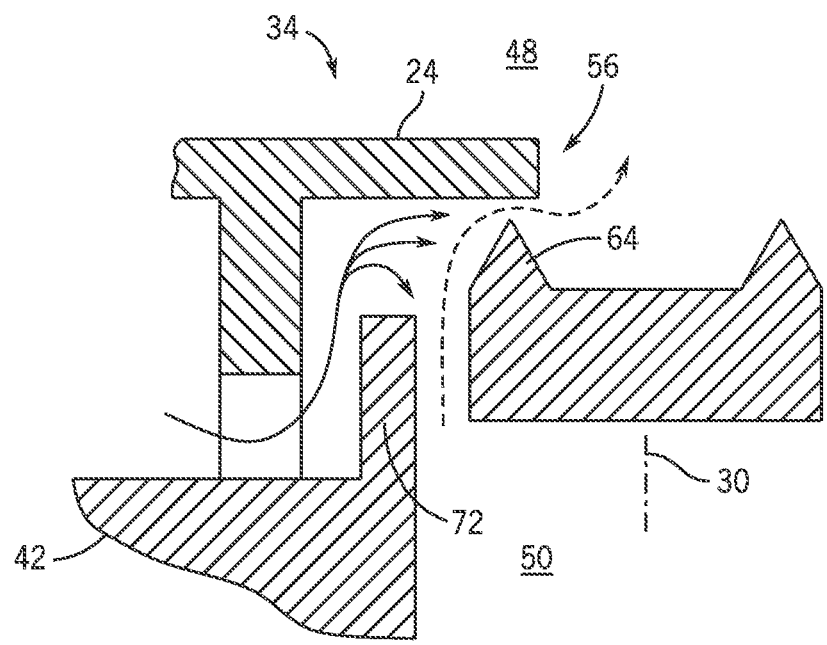
FIG. 11 is a fragmentary detail of alternative embodiment of the invention showing a diverter wall for reversing flow of infusion liquid for improved cleaning.

Referring now to FIG. 11 improved flushing, for example, of blood drawn in the aspiration mode of FIG. 9, may be provided through the use of the diverter wall 72, similar to diverter wall 53 of FIG. 6 but passing along axis 30 and serving to direct flow in an opposite direction of the flow received by upper channel 48 toward the interface between the inner periphery of opening 56 and the valve seat 64. Diverter wall 72 may be molded integrally with the housing 42 and also integrally molded with the valve seat 64. Essentially, diverter wall 72 changes the channel 70 shown in FIG. 10 to reverse flow direction just before it is received by lower channel 50.

Figure 12:
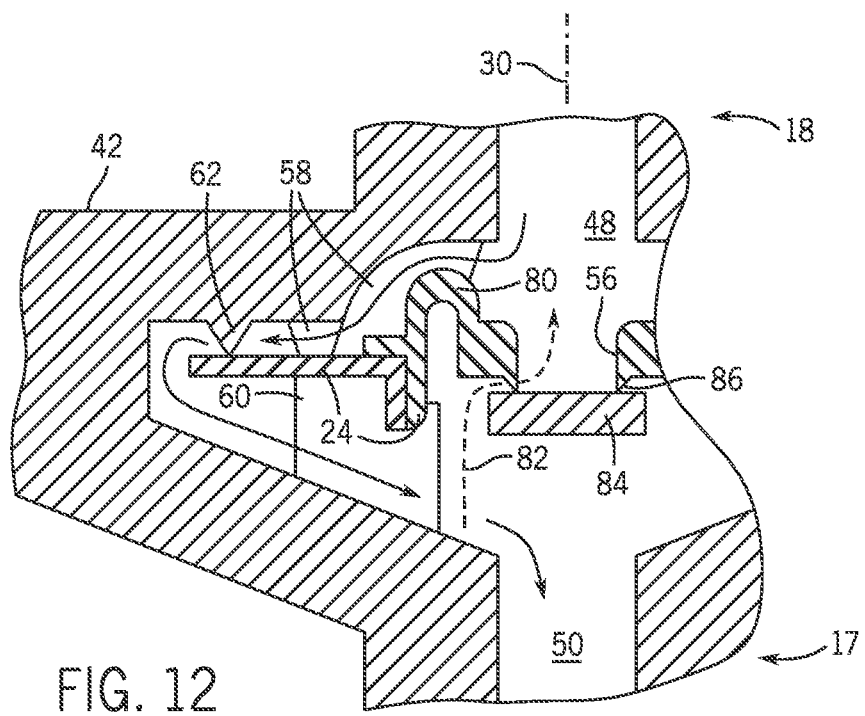
FIG. 12 is a fragmentary detail of an alternative embodiment of the invention showing a dual elastomeric disk.

Referring now to FIG. 12, in some embodiments, the elastomeric diaphragm 24 may be formed of two different elastomeric materials having different Shore hardnesses corresponding approximately to different elasticities of the materials. For example, the outer peripheral region 32 of the disk may be constructed of a relatively low hardness silicone elastomeric material whereas the central region 34 forming circular opening 56 may be constructed of a much harder silicone elastomeric material. The threshold opening pressures 47 and 49, shown in FIG. 7, are defined by the geometry of the valve and by the elasticity of the elastomeric diaphragm 24 in the central region 34 and the outer peripheral region 32 and thus adjusting the elasticity of these materials can provide an additional dimension of adjustment and provide a greater difference in threshold opening pressures. For example, it is believed this design can provide a low threshold opening pressure 49 of less than 20 millibars and a very high threshold opening pressure 47 of greater than two bars or approximately 100 times greater than the threshold opening pressure 49.

In the embodiment of FIG. 12, the geometry of the elastomeric diaphragm 24 about the opening 56 is changed substantially from a planar configuration shown in FIGS. 8-10 to provide a downwardly opening arch 80 whose inner leg forms a rim of opening 56. Aspirated flow 82 past valve seat 84 must provide for substantially both a bending and substantial compression of components of the material of the elastomeric diaphragm 24 as a result of this art form. To this end, the upper portion of the arch 80 may be supported by ribs 58 extending downward from an upper wall of the cavity 28 that serve to brace the arch against axial movement along axis 30. In this design, the valve seat 84 is substantially flat and a sharpened ridge 86 is formed on the lower surface of the periphery of opening 56 that seals against the flat surface of the valve seat 84.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

Various features of the invention are set forth in the following claims. It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

What is claimed is:

1. A valve for bidirectional flow comprising:
   a housing providing a first and second port communicating with an internal housing volume;
   an elastomeric disk positioned between the first and second port in the internal housing volume, the elastomeric disk retained against the housing so that the housing holds the elastomeric disk at a protruding annular location on the elastomeric disk between a central region and an outer peripheral region of the elastomeric disk so that the central region and outer peripheral region of the elastomeric disk are free to move with respect to the housing with a flow fluid;
   the housing providing a first valve seat engaging the outer peripheral region of the elastomeric disk when the elastomeric disk is in a relaxed state and having a second valve seat engaging the central region when the elastomeric disk is in a relaxed state;
   the housing further providing first flow channels leading from the first port to the elastomeric disk to press the elastomeric disk against the second valve seat and to press the elastomeric disk away from the first valve seat when pressure at the first port is greater than pressure at the second port; and
   the housing further providing second flow channels leading from the second port to the elastomeric disk to press the elastomeric disk against the first valve seat and to lift the elastomeric disk away from the second valve seat when pressure at the second port is greater than pressure at the first port.

2. The valve of claim 1 wherein the elastomeric disk interacts with the first and second valve seats to provide for a first threshold opening pressure at which fluid flows between the first port and the second port and a second threshold opening pressure different from the first threshold opening pressure when the fluid flows between the second port and the first port.

3. The valve of claim 2 wherein the first threshold opening pressure permits gravity flow of intravenous liquids from a standard IV bag.

4. The valve of claim 3 wherein the second opening pressure permits sampling of patient blood from a patient using a syringe or vacuum pump device.

5. The valve of claim 3 wherein the first threshold opening pressure is less than twenty millibars and the second threshold opening pressure is greater than two bars.

6. The valve of claim 2 wherein a difference between the first and second threshold opening pressures is a factor greater than one hundred.

7. The valve of claim 1 wherein the elastomeric disk is comprised of a first and second elastic material of different elasticity.

8. The valve of claim 1 wherein the elastomeric disk is comprised of a first and second elastic material of different Shore hardnesses.

9. The valve of claim 8 wherein the first elastic material of greater elasticity forms the outer peripheral region of the elastomeric disk contacting the first valve seat and the second elastic material of lesser elasticity forms the central region contacting the second valve seat.

10. The valve of claim 1 wherein the first flow channel substantially overlaps an entirety of the second flow channel to provide cleaning of the valve with flow from the first port.

11. The valve of claim 10 wherein fluid flow enters the first port in a first direction toward a first side of the elastomeric disk and wherein the first flow channels include diverter walls directing flow opposite the first direction toward a second side of the elastomeric disk.

12. The valve of claim 1 wherein the first and second ports are coaxial about a common axis and the elastomeric disk extends generally perpendicular to the common axis.

13. The valve of claim 12 wherein at least one of the first and second ports provides a connection adapted to standard luer locks or tube connections for IV sets.

14. The valve of claim 1 wherein the elastomeric disk between the first and second valve seats provides substantially circular and concentric contact lines between the valve seats and the elastomeric disk.

15. The valve of claim 1 wherein the first and second valve seats are ridges contacting opposite sides of the elastomeric disk.

16. The valve of claim 1 wherein the housing is assembled from multiple thermoplastic molded components.

17. A method of providing intravenous fluids to a patient and permitting sampling of patient blood using a valve for bidirectional flow of the type providing:
   a housing providing a first and second port communicating with an internal housing volume;
   an elastomeric disk positioned between the first and second port in the internal housing volume, the elastomeric disk retained against the housing so that the housing holds the elastomeric disk at a protruding annular location on the elastomeric disk between a central region and an outer peripheral region of the elastomeric disk so that the central region and outer peripheral region of the elastomeric disk are free to move with respect to the housing with a flow of fluid;
   the housing providing a first valve seat engaging the outer peripheral region of the elastomeric disk when the elastomeric disk is in a relaxed state and having a second valve seat engaging the central region when the elastomeric disk is in a relaxed state;
   the housing further providing first flow channels leading from the first port to the elastomeric disk to press the elastomeric disk against the second valve seat and to press the elastomeric disk away from the first valve seat when pressure at the first port is greater than pressure at the second port; and
   the housing further providing a second flow channels leading from the second port to the elastomeric disk to press the elastomeric disk against the first valve seat and to lift the elastomeric disk away from the second valve seat when pressure at the second port is greater than pressure at the first port;
   the method comprising the steps of:
   (a) connecting an IV line to a patient extending to the valve;
   (b) attaching the valve to an intravenous fluid source to provide flow from the intravenous fluid source through the valve and IV line to the patient; and
   (c) attaching the valve to a syringe to draw blood through the valve and IV line from the patient.

* * * * *